United States Patent [19]

Sauli

[11] 4,080,473
[45] Mar. 21, 1978

[54] DERIVATIVES OF 3-(3,5-DICHLOROPHENYL)-UREIDOACETIC ACID

[75] Inventor: Michel Sauli, Paris, France

[73] Assignee: Philagro, Lyon, France

[21] Appl. No.: 718,381

[22] Filed: Aug. 27, 1976

[30] Foreign Application Priority Data

Sep. 11, 1975    France ................. 75 27882

[51] Int. Cl.² ........................... C07C 127/22
[52] U.S. Cl. .............. 424/319; 260/518 A; 548/312; 548/308
[58] Field of Search .......... 260/518 A; 424/319

[56] References Cited

U.S. PATENT DOCUMENTS 3,808,262    4/1974    Zeeh et al. ............ 260/518 A

Primary Examiner—Vivian Garner
Attorney, Agent, or Firm—Browdy and Neimark

[57] ABSTRACT

Derivatives of 3-(3,5-dichlorophenyl)-ureidoacetic acid, of the general formula:

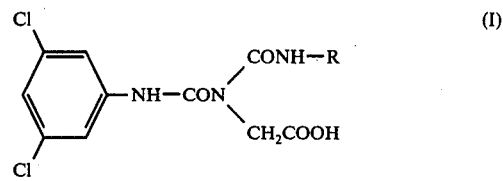

wherein R is a linear or branched alkyl radical containing 1 to 4 carbons, or an alkenyl of 2 to 4 carbons, is obtained by the action of an inorganic base such as sodium hydroxide, potassium hydroxide or ammonia, in an aqueous-organic solution such as a mixture of ethanol and water, on a hydantoin derivative of the general formula:

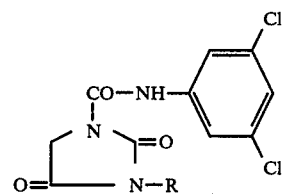

in which R is defined as above. The compounds (I) have fungicidal activity.

8 Claims, No Drawings

DERIVATIVES OF 3-(3,5-DICHLOROPHENYL)-UREIDOACETIC ACID

The present invention relates to new derivatives of 3-(3,5-dichlorophenyl)-ureidoacetic acid, of the general formula:

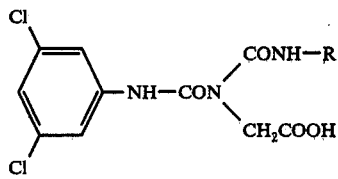
(I)

their preparation and the compositions in which they are present.

In the general formula (I), R represents a linear or branched alkyl radical contaning 1 to 4 carbon atoms, or an alkenyl radical containing 2 to 4 carbon atoms.

According to the invention, the new derivatives of the general formula (I) can be obtained by the action of an inorganic base such as sodium hydroxide, potassium hydroxide or ammonia, in an aqueous-organic solution such as a mixture of ethanol and water, on a hydantoin derivative of the general formula:

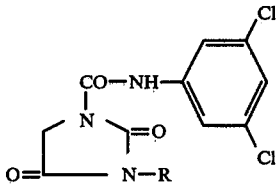
(II)

in which R is defined as above.

The process is generally carried out at a temperature of between 20° and 80° C.

The hydantoin derivative of the general formula (II) can be obtained by the action of 3,5-dichlorophenyl isocyanate on a hydantoin of the general formula:

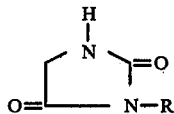
(III)

in which R is defined as above.

The hydantoin derivative of the general formula (III) can be obtained by cyclisation of an acid of the general formula:

 R—NH—CO—NH—CH$_2$—COOH (IV)

in which R is defined as above, in an organic medium such as chlorobenzene, in the presence of a dehydrating agent.

The acid of the general formula (IV) can be obtained by the action of an isocyanate of the general formula:

 R—N=C=O (V)

in which R is defined as above, on glycine.

The new products according to the invention can optionally be purified by physical methods such as crystallisation or chromatography.

The examples which follow are given, without implying a limitation, to illustrate the preparation and the fungicidal properties of the compounds according to the invention.

EXAMPLE 1

10 N Sodium hydroxide (80 cc.) and water (50 cc.) are added gradually to a suspension of 1-(3,5-dichlorophenyl)-carbamoyl-3-isopropyl-hydantoin (16.5 g.) in ethanol (80 cc.). The reaction mixture is heated to about 60° C, whilst stirring. It is then pouring into water (one litre) and the suspension obtained is filtered in the presence of decolorising charcoal. The limpid filtrate is then poured, whilst stirring, on to a mixture of hydrochloric acid ($d = 1.19$) (100 cc.) and crushed ice (300 g.). The mixture is then extracted with isopropyl ether (300 cc. followed by 100 cc.). The organic solution is dried and concentrated to dryness under reduced pressure. The oily residue obtained (14 g.) is crystallised from a mixture of isopropyl ether (100 cc.) and petroleum ether (boiling point = 35°-60° C) (100 cc.). 2-[3-(3,5-Dichlorophenyl)-1-isopropylcarbamoyl-ureido]-acetic acid (12 g.), melting, with decomposition, at 175° C, is thus obtained.

3-Isopropyl-1-(3,5-dichlorophenyl)-carbamoyl-hydantoin can be prepared in the following manner.

A solution of 3,5-dichlorophenyl isocyanate (71.5 g.) in acetone (250 cc.), and triethylamine (38.4 g.) are added successively, whilst stirring, to a solution of 3-isopropyl-hydantoin (56.8 g.) in acetone (250 cc.). The temperature of the reaction mixture rises gradually from 25° C to 50° C over the course of 20 minutes and then again drops, whilst a copious precipitate forms. The reaction mixture is stirred for a further 5 hours at a temperature of about 20° C. The precipitate is filtered off, washed with acetone (2 × 50 cc.) and then dried under reduced pressure. 1-(3,5-Dichlorophenyl)-carbamoyl-3-isopropyl-hydantoin (100 g.) melting at 200° C, is thus obtained.

3-Isopropyl-hydantoin can be prepared in the following manner.

A suspension of 2-(3-isopropylureido)-acetic acid (64 g.) in chlorobenzene (250 cc.) is heated at 90° C, and sulphuric acid ($d = 1.83$) (4 cc.) is then added to this suspension. The reaction mixture is heated gradually to about 110° C, with constant stirring. The water formed is separated off by azeotropic distillation. The distillation is stopped when the temperature of the vapours reaches 126° C. The reaction mixture is cooled and potassium carbonate (10 g.), followed by distilled water (20 cc.) are added successively, the water being added with appropriate precautions. After the evolution of carbon dioxide has ceased, potassium carbonate (20 g.) is also added and stirring is continued for one hour. The reaction mixture is diluted with methylene chloride (300 cc.), the aqueous phase is decanted and the organic phase is dried over anhydrous sodium sulphate. After filtration, and concentration under reduced pressure, 3-isopropyl-hydantoin (56.8 g.), melting at 86° C is obtained.

2-(3-Isopropylureido)-acetic acid can be prepared in the following manner.

A solution of glycine (75.1 g.) in normal sodium hydroxide solution (one litre) is heated at 36° C. A solution of isopropyl isocyanate (76.5 g.) in acetone (100 cc.) is then added dropwise, whilst stirring. A rise in temperature from 36° to 50° C is observed in the course of the addition. The reaction mixture is stirred for a further 30 minutes after the end of the addition. Crushed ice (500 g.) and water (250 cc.) are then added and the mixture is acidified by adding 5 N hydrochloric acid (200 cc.), while stirring. The precipitate is then filtered off, and dried. 2-(3-Isopropylureido)-acetic acid (70 g.) melting at 178° C is thus obtained. A second crop (44 g.) of 2-(3-isopropylureido)-acetic acid, melting at 178° C, is obtained by concentrating the filtrate.

EXAMPLE 2

In Vitro Test of the Fungicidal Activity

For this experiment, a series of test tubes each containing an artificial culture medium (Sabouraud agar) (4 ml.) is used.

After sterilisation in an autoclave, a suspension (2 ml.) containing the active material at various concentrations (of active material), is added to each tube.

A suspension of spores in sterile distilled water is prepared for various species of fungi; the suspension contains $4 \times 10^6$ spores/ml., and each tube is inoculated with 0.25 ml. of this suspension. After inoculation, the tubes are kept in an oven at 25° C for 9 days.

On the ninth day of the culture, the percentage inhibition of the growth of each species of fungus is evaluated for various concentrations of active material. From these results, the minimum concentration of the product which causes 95 to 100% inhibition of the growth of the fungi, which is called the "minimum inhibitory concentration", is determined for each species of fungus. This concentration is expressed in μg of active material per ml. of suspension; the results relating to the compound of Example 1 are summarized in the table below:

| Fungi | Minimum inhibitory concentration (μg./ml.) |
|---|---|
| Fusarium oxysporum | 500 |
| Botrytis cinerea | 6 |
| Penicillium digitatum | 20 |
| Aspergillus niger | 25 |
| Alternaria mali | 5 |
| Helminthosporium graminearum | 8 |

EXAMPLE 3

Test on Bean Anthrachnose

Bean plants (*Phaseolus vulgaris*), Michelet variety, are cultivated in pots. When these plants are about 12 days old (the stage at which the cotyledon leaves are completely developed), they are treated by spraying the 4 ml., per plant, of an aqueous suspension which contains the active material at the desired concentration, and also contains as a wetting agent 0.02% of a condensate of sorbitol monooleate with 10 mols of ethylene oxide. Each concentration is repeated eight times. The comparison plants are treated under the same conditions, but without active material. After drying for 4 hours, each plant is infested with a suspension of spores (1 ml., containing $10^6$ spores) of *Colletotrichum lindemuthianum*, responsible for bean anthrachnose, and the plants are then incubated for 7 days at about 22° C and 80% relative humidity.

At the end of seven days after infestation the minimum concentration which brings about 95-100% inhibition of the parasite is determined.

Under these conditions it is found that for the compound of Example 1, this concentration is 2,000 μg/ml.

EXAMPLE 4

Test on Wheat Rust

The procedure of Example 3 is followed except that the plants are young wheat plants (Triticum sativum), Etoile de Choisy variety, cultivated at the rate of 50 per pot. They are treated, at the age of about seven days, at the single-leaf stage (height = 9–10 cm.), and infested with uredospores of *Puccinia glumarum*, responsible for wheat rust.

Under these conditions it is found that for the compound of Example 1 the minimum inhibitory concentration for the fungus is 750 μg/ml.

EXAMPLE 5

Test on Grey Mould Rot of Grapes

Ripe and healthy individual grapes (Chasselas variety) are detached from a bunch, disinfected with mercuric chloride, washed, dried and arranged, at the rate of 12 grapes per dish, in Petri dishes, the bottom of which is covered with sand. The grapes are then damaged by pricking them with a needle in 4 different places. Infestation is then carried out by spraying with a suspension of spores (500,000 spores/ml.) of *Botrytis cinerea*, responsible for grey mould rot of grapes. After drying for 4 hours, the grapes are treated by spraying with an aqueous suspension which contains the active material at the desired concentration and also contains as wetting agent 0.02% of a condensate of sorbitol monooleate with 10 mols of ethylene oxide. Incubation is carried out at 18° C in an atmosphere saturated with moisture, for 28 days after the infestation. The minimum concentration which produces 95–100% inhibition of the fungus is determined.

Under these conditions it is found that for the compound of Example 1, this concentration is 750 μg/ml.

These examples show clearly the excellent fungicidal activity of the compounds according to the invention against fungi belonging to a variety of families such as especially Ascomycetes (*Fusarium sp. Botrytis cinerea, Aspergillus niger, Penicillum digitatum* and the like), Basidiomycetes (*Puccinia glumarum* and the like) and Fungi imperfecti (*Alternaria sp., Helminthosporum graminaeum* and the like).

Furthermore, during these tests, no phytotoxicity was found.

The compounds according to the invention can consequently be used, in the form of compositions which also form part of the invention, for combating fungal diseases of plants and in particular of vine, strawberry plants, fruit trees and market-garden cultures. The compositions in general contain from 0.005 to 95% by weight of a compound according to the invention as the active material and are used, at the rate of 0.5 to 5 kg. of active material per hectare, and at concentrations ranging from 0.01 to 5 g. of active compound/1.

For practical use, the compounds according to the invention are generally employed in association with at least one carrier or diluent and/or at least one surface-active agent which is compatible with the active material and suitable for its use in agriculture.

The term "carrier" in the sense of the present description denotes an organic or inorganic, natural or synthetic, material with which the active material is associated to facilitate its application to the plant, to seeds or to the soil, or its transport or its handling. The carrier can be solid (clays, kaolin, bentonite, natural silicates, such as talc, or synthetic silicates, calcined magnesia, kieselguhr, tricalcium phosphate, cork powder, absorbent charcoal, resins, waxes, solid fertilisers or the like) or fluid (water, alcohols, ketones, petroleum fractions, chlorinated hydrocarbons or liquefied gases).

The surface-active agent can be an emulsifier, dispersing agent or wetting agent, and these can be ionic or non-ionic. By way of example there may be mentioned salts of polyacrylic acids and of liqninsulphonic acids, sulphoricinoleates, quaternary ammonium salts, condensates of ethylene oxide with fatty alcohols, fatty acids or fatty amines and especially products based on condensates of ethylene oxide such as the condensates of ethylene oxide with octylphenol, or esters of fatty acids of anhydro-sorbitols which have been solubilised by etherification of the free hydroxyl radicals by condensation with ethylene oxide. It is preferable to use agents of the non-ionic type because these are not sensitive to electrolytes.

The compositions according to the invention can be prepared in the form of wettable powders, dusting powders, granules, solutions, emulsifiable concentrates, emulsions, suspension concentrates and aerosols.

The wettable powders according to the invention can be prepared, for example, by grinding the active material with the solid carrier so that they contain from 20 to 95% by weight of the active material; they usually contain from 3 to 10% by weight of a dispersing agent and, where necessary, from 0 to 10% by weight of one or more stabilisers and/or other adjuvants such as penetrating agents, adhesives, anti-caking agents, dyestuffs and the like.

By way of example, the composition of a wettable powder is given below, the percentages being expressed by weight:

Active material, compound of formula I: 50%
Calcium lignosulphate (deflocculating agent): 5%
Isopropylnaphthalenesulphonate (wetting agent): 1%
Silica anti-caking agent: 5%
Kaoline filler: 39%

The powders for the treatment of seeds for dusting are usually prepared in the form of a dust concentrate having a composition similar to that of a wettable powder, but without a dispersing agent; they can be diluted, at the use site, by means of a supplementary amount of a fluid carrier, so that a composition is obtained which can conveniently coat the seeds to be treated and which usually contains from 0.5 to 10% by weight of active material.

By way of example, the composition of a powder for the treatment of seeds is given below:

Active material: compound of formula I: 50%
Anionic wetting agent: 1%
Silica anti-caking agent: 6%
Kaolin (filler): 43%

The emulsifiable concentrates which can be applied, by spraying, after dilution with water usually contain the active material in solution in a solvent and, in addition to the solvent and — where necessary — a co-solvent, from 10 to 50% by weight/volume of active material and from 2 to 20% by weight/volume of appropriate additives, such as stabilisers, penetrating agents, corrosion inhibitors, dyestuffs and adhesives.

By way of example, the composition of an emulsifiable concentrate is given below, the amounts being expressed in g/liter.

Active material: compound of formula I: 400 g/l.
Dodecylbenzenesulphonate: 24 g/l.
Nonylphenol oxyethylated with 10 molecules of ethylene oxide: 16 g/l.
Cyclohexanone: 200 g/l.
Aromatic solvent: q.s.p. 1 liter The suspension concentrates, which can also be applied by spraying, are prepared so that a stable fluid product which does not sediment is obtained, and they usually contain from 10 to 75% by weight of active material, from 0.5 to 15% by weight of surface-active agents, from 0.1 to 10% by weight of anti-sedimentation agents such as protective colloids and thixotropic agents, from 0 to 10% by weight of appropriate additives, such as anti-foam agents, corrosion inhibitors, stabilisers, penetrating agents and adhesives and, as the carrier, water or an organic liquid in which the active material is substantially insoluble; certain organic solid materials or inorganic salts can be dissolved in the carrier to assist in preventing the sedimentation or to act as antifreeze agents for the water.

Aqueous dispersions and emulsions, for example compositions obtained by diluting a wettable powder or an emulsifiable concentrate according to the invention with water, at the rate of 10 to 100 g. of active material per hectoliter of water, fall within the general scope of the present invention. These emulsions can be of the water-in-oil type or of the oil-in-water type and can have a thick consistency such as that of a "mayonnaise".

The compositions according to the invention can contain other ingredients, for example protective colloids, adhesives or thickeners, thixotropic agents, stabilisers or sequestering agents, as well as other known active materials having pesticidal properties, in particular insecticides or fungicides.

It will be obvious to those skilled in the art that various changes may be made without departing from the scope of the invention and the invention is not to be considered limited to what is described in the specification.

What is claimed is:

1. A derivative of 3-(3,5-dichlorophenyl)-ureidoacetic acid, having the formula

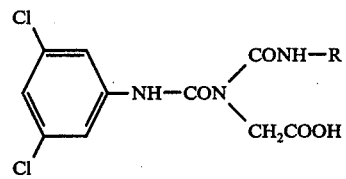

wherein R is alkyl of 1 to 4 carbons in a straight or branched chain.

2. A compound according to claim 1, wherein R is isopropyl.

3. A fungicidal composition for combating fungal diseases of plants, comprising, as the active product, at least one derivative of 3-(3,5-dichlorophenyl)-ureidoacetic acid having the formula

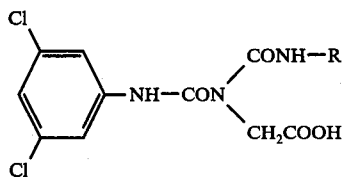

wherein R is alkyl to 1 to 4 carbons in a straight or branched chain, in a fungicidally effective amount, in association with one or more compatible carriers which can be used in agriculture.

4. A composition according to claim 3, characterized in that it contains from 0.005 to 95% by weight of fungicidally active product.

5. A composition in accordance with claim 3 wherein R is isopropyl.

6. A method for combating fungal diseases of plants comprising applying to said plant a fungicidally effective amount of a derivative of 3-(3,5-dichlorophenyl)-ureidoacetic acid, having the formula

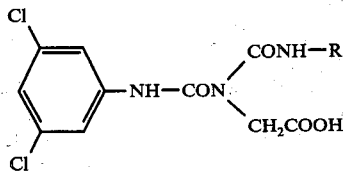

wherein R is alkyl of 1-4 carbons in a straight or branched chain.

7. A method in accordance with claim 6, wherein R is isopropyl.

8. A method in accordance with claim 6 wherein said compound is applied to seeds to said plants.

* * * * *